(12) United States Patent
Hu et al.

(10) Patent No.: US 12,054,454 B1
(45) Date of Patent: Aug. 6, 2024

(54) METHOD FOR CATALYZING OLEFIN CARBONYLATION

(71) Applicant: NANJING INSTITUTE OF MICROINTERFACE TECHNOLOGY CO., LTD, Jiangsu (CN)

(72) Inventors: Xingbang Hu, Jiangsu (CN); Zhibing Zhang, Jiangsu (CN); Chenfei Yao, Jiangsu (CN); Lei Li, Jiangsu (CN); Zheng Zhou, Jiangsu (CN)

(73) Assignee: NANJING INSTITUTE OF MICROINTERFACE TECHNOLOGY CO., LTD, Jiangsu (CN)

( * ) Notice: Subject to any disclaimer, the term of this patent is extended or adjusted under 35 U.S.C. 154(b) by 0 days.

(21) Appl. No.: 18/682,658

(22) PCT Filed: Nov. 16, 2021

(86) PCT No.: PCT/CN2021/130913
§ 371 (c)(1),
(2) Date: Feb. 9, 2024

(87) PCT Pub. No.: WO2023/070760
PCT Pub. Date: May 4, 2023

(30) Foreign Application Priority Data

Oct. 27, 2021 (CN) .......................... 202111256876.9

(51) Int. Cl.
*C07C 45/50* (2006.01)
*B01J 31/22* (2006.01)

(52) U.S. Cl.
CPC .......... *C07C 45/505* (2013.01); *B01J 31/2273* (2013.01); *B01J 2231/321* (2013.01); *B01J 2531/0233* (2013.01); *B01J 2531/827* (2013.01); *C07C 2531/22* (2013.01)

(58) Field of Classification Search
CPC ................. C07C 45/505; B01J 31/2273; B01J 2231/321; B01J 2531/827
See application file for complete search history.

(56) References Cited

U.S. PATENT DOCUMENTS

| | | | | |
|---|---|---|---|---|
| 5,227,522 A | * | 7/1993 | Denis .................... | C07C 51/14 562/522 |
| 5,420,346 A | * | 5/1995 | Denis .................... | C07C 51/14 562/522 |
| 5,847,204 A | | 12/1998 | Nobel | |
| 2016/0068458 A1 | | 3/2016 | Mandimutsira et al. | |

FOREIGN PATENT DOCUMENTS

| | | |
|---|---|---|
| CN | 104001548 | 8/2014 |
| CN | 111068785 | 4/2020 |
| CN | 112457178 | 3/2021 |
| GB | 1367623 | 9/1974 |

OTHER PUBLICATIONS

International Search Report—ISA/CN; PCT/CN2021/130913; Mailed Jul. 27, 2022; 3 pgs.

\* cited by examiner

*Primary Examiner* — Sikarl A Witherspoon
(74) *Attorney, Agent, or Firm* — Chun-Ming Shih; LANWAY IPR SERVICES

(57) ABSTRACT

The present invention discloses a method for catalyzing olefin carbonylation, including the following steps: using cyclic alkylcarbene iridium as a catalyst and an olefin as a raw material to carry out carbonylation reaction to generate aldehydes, wherein a structural formula of the cyclic alkylcarbene iridium is as follows:

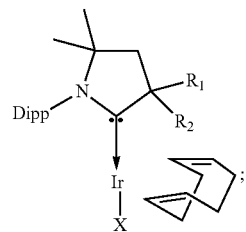

wherein Dipp is 2,6-diisopropylbenzene; R1 and R2 are methyl or ethyl; X is Cl, Br, CH3CO2, NO3, BF4, PF6 or SbF6; wherein the olefin comprises one or more of ethylene, propylene, butylene and higher carbon olefins. According to the method for catalyzing olefin carbonylation of the present invention, by adopting an iridium catalyst, the catalytic activity is good, reaction energy consumption is reduced, and reaction temperature is fully lowered.

12 Claims, 2 Drawing Sheets

METHOD FOR CATALYZING OLEFIN CARBONYLATION

FIELD OF THE INVENTION

The present invention relates to the field of carbonylation reactions, and specifically to a method for catalyzing olefin carbonylation.

BACKGROUND OF THE INVENTION

Butanol and octanol are very widely used bulk chemical raw materials. At present, the industrial synthesis of butyl octanol is mainly through the hydroformylation of propylene to produce n-butyraldehyde and isobutyraldehyde, and then they are used as raw materials for subsequent reactions. The hydroformylation reaction of propylene is a key step in the synthesis of butyl octanol.

So far, there have been many patents reported on the hydroformylation of propylene to synthesize n-butyraldehyde and isobutyraldehyde. These patents, as well as current industrial methods, commonly use catalysts based on metal rhodium. For example, patents WO0200583, EP3712126A1, and CN102826967A use triphenylphosphorus-rhodium as catalyst; a patent JP2002047294 uses cyclooctadiene acetate-rhodium as catalyst; a patent CN110156580 uses 6,6'-((3,3'-di-tert-butyl-5,5'-dimethoxy-[1,1'-biphenyl]-2, bis(oxy))diphenyl and [d,f] [1,3,2]dioxaphospholene-rhodium as catalyst; a patent CN103896748A uses acetylmorpholine-rhodium as catalyst; a patent EP3770144A1 uses acetate-rhodium as catalyst; a patent CN11348995A uses tris [2,4-di-tert-butylphenyl] phosphite-rhodium as catalyst; a patent U.S. Pat. No. 9,550,179 uses long-chain carboxylic acid-rhodium as the catalyst; a patent CN102826973A uses acetylacetone carbonyl-rhodium as catalyst; a patent EP2417094B1 uses triphenylphosphine carbonyl rhodium hydride as catalyst; and a patent EP2417093B1 uses rhodium dimer acetate and triphenyl phosphonium tri sulfonate sodium salt as catalyst. Because metal rhodium has high catalytic activity in the hydroformylation reaction of propylene, the reaction conditions of reaction systems using this as a catalyst are generally mild. Typical reaction temperatures are between 90-132° C., and typical reaction pressures are between 1.6-5 MPa (see Table 1).

Although rhodium metal can be recycled many times in the propylene hydroformylation reaction, the slow loss and deactivation are inevitable. Due to the rapid increase in international rhodium metal prices, the cost of catalysts in the corresponding process has also increased rapidly.

TABLE 1

Reaction pressures of existing technologies.

| Patent Number | Typical reaction temperature (° C.) | Typical reaction pressure (MPa) |
|---|---|---|
| CN110156580 | 90 | 1.6 |
| CN103896748A | 80-130 | 2-6 |
| EP3770144A1 | 126 | 5 |
| CN111348995A | 90-130 | 4-6 |
| EP 3712126A1 | 110 | 5 |
| US 9550179 | 95 | 1.8 |
| CN102826967A | 90 | 1.8 |
| CN 102826973 A | 90 | 1.9 |

TABLE 1-continued

Reaction pressures of existing technologies.

| Patent Number | Typical reaction temperature (° C.) | Typical reaction pressure (MPa) |
|---|---|---|
| EP2417094B1 | 132 | 5 |
| EP2417093B1 | 122 | 5 |

In view of this, the present invention is proposed.

SUMMARY OF TILE INVENTION

A first objective of the present invention is to provide a method for catalyzing olefin carbonylation. The method combines highly active carbene ligands with metal iridium and uses coordination anions to further adjust the catalyst performance, which gives the catalyst a good catalytic activity. It can lower the reaction temperature, reduce energy consumption and reduce costs.

In order to achieve the above objectives of the present invention, the following technical schemes are adopted.

The method provides a method for catalyzing olefin carbonylation, including the following steps:

using cyclic alkylcarbene iridium as a catalyst and olefin as a raw material to carry out carbonylation reaction to generate aldehydes, wherein a structural formula of the cyclic alkylcarbene iridium is as follows:

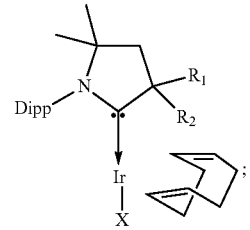

wherein Dipp is 2,6-diisopropylbenzene; $R_1$ and $R_2$ are methyl or ethyl; X is Cl, Br, $CH_3CO_2$, $NO_3$, $BF_4$, $PF_6$ or $SbF_6$;

wherein the olefin includes one or more of ethylene, propylene, butylene and higher carbon olefins.

The above-mentioned catalyst can be preferably used in the process of the olefin carbonylation reaction, and compared with previous rhodium catalysts, its cost is low, its activity is good, and its catalytic effect is good.

Preferably, as a further embodiment, a reaction solvent includes a mixture of one or more of n-butyraldehyde, isobutyraldehyde, toluene, benzene and tetrahydrofuran.

Preferably, as a further embodiment, a dosage of the catalyst is 0.005-2 wt % of a dosage of the reaction solvent, preferably 0.05-1 wt %.

Preferably, as a further embodiment, the olefin is propylene, and the other raw materials include carbon monoxide and hydrogen, and a total reaction pressure is between 0.5-5.0 MPa, preferably between 1.0-3.0 MPa. A total reaction pressure can be 0.6 MPa, 0.7 MPa, 0.8 MPa, 0.9 MPa. 1.0 MPa, etc.

Preferably, as a further embodiment, a reaction temperature is between 60~180° C., preferably between 80° C.~140° C. The reaction temperature can be 60° C., 70° C., 80° C. or 90° C.

The scheme of the present invention is more suitable for propylene hydroformylation reaction, and can obtain better reaction effect between the reaction temperature of 60~180° C. and the reaction pressure of 0.5-5.0 MPa. At the same time, the price of iridium metal is only about one-third of that of rhodium metal. Equivalently, the present invention provides an economical and mild new method for synthesizing n-butyraldehyde and isobutyraldehyde through propylene hydroformylation reaction.

Preferably, as a further embodiment, a partial pressure ratio of propylene to carbon monoxide is between 1:1-1:10, preferably between 1:2-1:5.

Preferably, as a further embodiment, a partial pressure ratio of propylene to hydrogen is between 1:1-1:10, preferably between 1:2-1:5.

By controlling each operating parameter in the above reaction process within an appropriate proportion range can significantly improve the reaction effect.

Compared with the prior art, the beneficial effects of the present invention are:

(1) The carbonylation reaction method of the present invention uses highly active carbene ligands to coordinate metal iridium and adopts coordination anions to further adjust the catalyst performance, which gives the catalyst a good catalytic activity.

(2) The catalytic reaction temperature of the present invention is low, the energy consumption is low, and the cost of the catalyst used is also low.

BRIEF DESCRIPTION OF THE DRAWINGS

Various other advantages and benefits will become apparent to those of ordinary skill in the art upon reading the following detailed description of the preferred embodiments. The drawings are for the purpose of illustrating preferred embodiments only and are not to be construed as limiting the present invention. Also, throughout the drawings, the same reference characters are used to designate the same components. In the drawings.

DESCRIPTION OF THE PREFERRED EMBODIMENTS

The schemes of the present invention will be described in detail below with reference to embodiments, however, those skilled in the art will understand that the following embodiments are only used to illustrate the present invention and should not be regarded as limiting the scope of the present invention.

If the specific conditions are not specified in the embodiments, the conditions should be carried out according to the conventional conditions or the conditions recommended by the manufacturer. If the manufacturer of the reagents or instruments used is not indicated, they are all conventional products that can be purchased commercially.

Embodiment 1

Figure 1:
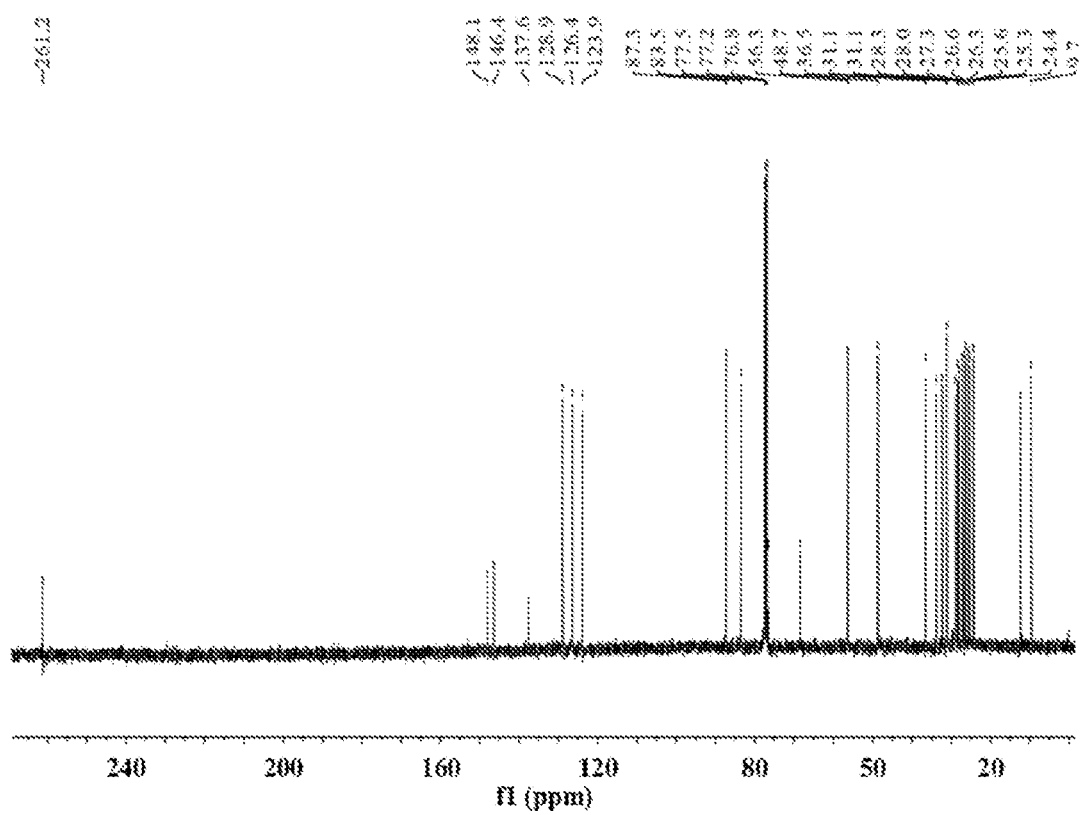
FIG. 1 is a nuclear magnetic resonance carbon spectrum diagram of the catalyst CAAC (C 2C 2)-Ir—Cl provided in Embodiment 1 of the present invention.
Figure 2:
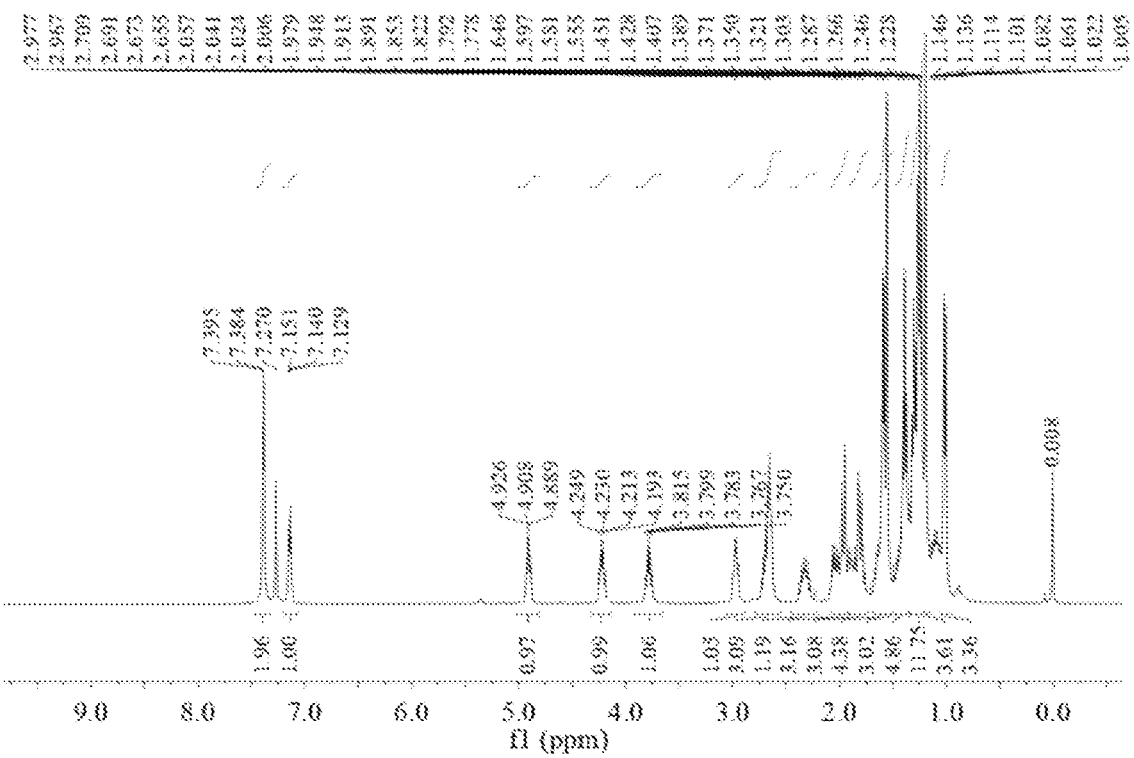
FIG. 2 is a nuclear magnetic resonance hydrogen spectrum diagram of the catalyst CAAC (C 2C 2)-Ir—Cl provided in Embodiment 1 of the present invention.

In a 50 ml high-pressure reaction kettle, add 10 ml of toluene solution containing 0.25 wt % CAAC (C 2 C 2)-Ir—Cl. After hydrogen replacement three times, 3 bar propylene, 8 bar carbon monoxide, and 8 bar hydrogen are introduced in sequence, and the temperature is raised to 90° C. with stirring. The reaction is stirred at this temperature for 8 hours, and the reaction solution is cooled to 0° C. After slowly releasing the pressure, samples are taken for gas chromatography analysis. The results show that the propylene conversion rate is 92.1%, and the selectivity of n-butyraldehyde and isobutyraldehyde is 99.9% (n-butyraldehyde:isobutyraldehyde=3.3:1). The confirmed nuclear magnetic resonance hydrogen spectrum diagram and the nuclear magnetic resonance carbon spectrum diagram of the catalyst used in the specific embodiment are shown in FIG. 1-FIG. 2.

Embodiments 2-7

The propylene hydroformylation reaction method of Embodiment 1 is adopted while changing the coordination anion of CAAC(C2C2)-Ir—X ions, and the results are shown in Table 2.

TABLE 2

Effects of coordination anions of CAAC(C2C2)-Ir-X on propylene hydroformylation reaction.

| Embodiment | X | Propylene conversion rate (%) | Selectivity of n-butyraldehyde and isobutyraldehyde (%) | n-butyraldehyde:isobutyraldehyde |
|---|---|---|---|---|
| 2 | Br | 92.6 | 99.9 | 3.5:1 |
| 3 | $CH_3CO_2$ | 90.7 | 99.9 | 5.3:1 |
| 4 | $NO_3$ | 86.5 | 99.9 | 4.1:1 |
| 5 | $BF_4$ | 93.9 | 99.9 | 5.6:1 |
| 6 | $PF_6$ | 92.3 | 99.9 | 6.5:1 |
| 7 | $SbF_6$ | 94.6 | 99.9 | 7.2:1 |

Embodiments 8-12

The propylene hydroformylation reaction method of Embodiment 1 is adopted while changing different temperatures to carry out the reaction, and the results are shown in Table 3.

TABLE 3

Effects of temperature on propylene hydroformylation reaction.

| Embodiment | Temperature (° C.) | Propylene conversion rate (%) | Selectivity of n-butyraldehyde and isobutyraldehyde (%) | n-butyraldehyde:isobutyraldehyde |
|---|---|---|---|---|
| 8 | 60 | 92.7 | 99.9 | 3.2:1 |
| 9 | 80 | 93.1 | 99.9 | 3.2:1 |
| 10 | 100 | 93.2 | 99.9 | 3.3:1 |
| 11 | 120 | 93.6 | 99.9 | 3.3:1 |
| 12 | 140 | 94.1 | 99.9 | 3.4:1 |

Embodiments 13-16

The propylene hydroformylation reaction method of Embodiment 1 is adopted while changing the pressure of gas, and the results are shown in Table 4.

TABLE 4

Effects of pressure on propylene hydroformylation reaction.

| Embodiment | Acrylic (bar) | CO (bar) | H$_2$ (bar) | Propylene conversion rate (%) | Selectivity of n-butyraldehyde and isobutyraldehyde (%) | n-butyraldehyde: isobutyraldehyde |
|---|---|---|---|---|---|---|
| 13 | 3 | 4 | 4 | 92.2 | 99.9 | 3.5:1 |
| 14 | 3 | 6 | 6 | 92.5 | 99.9 | 3.3:1 |
| 15 | 3 | 10 | 10 | 93.5 | 99.9 | 3.2:1 |
| 16 | 3 | 12 | 12 | 95.1 | 99.9 | 3.2:1 |

As can be seen from the above tables that: by using iridium catalyst for catalytic reaction, even under low-temperature and low-pressure conditions, it still has good reaction selectivity and good reaction conversion rate. Therefore, the present invention adopts a new catalyst to carry out the catalytic reaction and explores the reaction conditions, thereby realizing the reaction under the conditions of low energy consumption and high reaction efficiency.

Finally, it should be noted that the above embodiments are only used to illustrate the technical schemes of the present invention, rather than to limit the present invention. Although the present invention has been described in detail with reference to the above-mentioned embodiments, those of ordinary skill in the art should understand that they can still modify the technical schemes recorded in the above-mentioned embodiments or make equivalent substitutions for some or all of the technical features. However, these modifications or substitutions do not cause the essence of the corresponding technical scheme to depart from the scope of the technical scheme of each embodiment of the present invention.

What is claimed is:

1. A method for catalyzing olefin carbonylation, comprising the following steps:
   using cyclic alkylcarbene iridium as a catalyst and olefin as a raw material to carry out carbonylation reaction to generate aldehydes, wherein a structural formula of the cyclic alkylcarbene iridium is as follows:

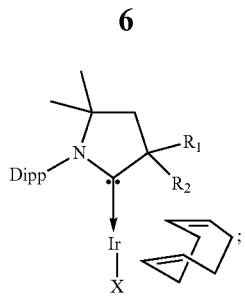

wherein Dipp is 2,6-diisopropylbenzene; $R_1$ and $R_2$ are methyl or ethyl; X is Cl, Br, CH$_3$CO$_2$, NO$_3$, BF$_4$, PF$_6$ or SbF$_6$;
   wherein the olefin comprises one or more of ethylene, propylene, butylene and higher carbon olefins.

2. The method for catalyzing olefin carbonylation according to claim 1, wherein a reaction solvent includes a mixture of one or more of n-butyraldehyde, isobutyraldehyde, toluene, benzene and tetrahydrofuran.

3. The method for catalyzing olefin carbonylation according to claim 2, wherein a dosage of the catalyst is 0.005-2 wt % of a dosage of the reaction solvent.

4. The method for catalyzing olefin carbonylation according to claim 2, wherein a dosage of the catalyst is 0.05-1 wt % of a dosage of the reaction solvent.

5. The method for catalyzing olefin carbonylation according to claim 1, wherein the olefin is propylene, and the other raw materials comprise carbon monoxide and hydrogen, and a total reaction pressure is between 0.5-5.0 MPa.

6. The method for catalyzing olefin carbonylation according to claim 1, wherein a total reaction pressure is between 1.0-3.0 MPa.

7. The method for catalyzing olefin carbonylation according to claim 5, wherein a partial pressure ratio of propylene to carbon monoxide is between 1:1-1:10.

8. The method for catalyzing olefin carbonylation according to claim 5, wherein a partial pressure ratio of propylene to carbon monoxide is between 1:2-1:5.

9. The method for catalyzing olefin carbonylation according to claim 5, wherein a partial pressure ratio of propylene to hydrogen is between 1:1-1:10.

10. The method for catalyzing olefin carbonylation according to claim 5, wherein a partial pressure ratio of propylene to hydrogen is between 1:2-1:5.

11. The method for catalyzing olefin carbonylation according to claim 5, wherein a reaction temperature is between 60-180° C.

12. The method for catalyzing olefin carbonylation according to claim 5, wherein a reaction temperature is between 80° C.~140° C.

* * * * *